(12) United States Patent
Sankaranarayanan et al.

(10) Patent No.: US 10,839,195 B2
(45) Date of Patent: Nov. 17, 2020

(54) MACHINE LEARNING TECHNIQUE TO IDENTIFY GRAINS IN POLYCRYSTALLINE MATERIALS SAMPLES

(71) Applicant: UCHICAGO ARGONNE, LLC, Chicago, IL (US)

(72) Inventors: Subramanian Sankaranarayanan, Naperville, IL (US); Mathew J. Cherukara, Lemont, IL (US); Badri Narayanan, Lemont, IL (US); Henry Chan, Lemont, IL (US)

(73) Assignee: UChicago Argonne, LLC, Chicago, IL (US)

( * ) Notice: Subject to any disclaimer, the term of this patent is extended or adjusted under 35 U.S.C. 154(b) by 634 days.

(21) Appl. No.: 15/672,168

(22) Filed: Aug. 8, 2017

(65) Prior Publication Data

US 2019/0050628 A1 Feb. 14, 2019

(51) Int. Cl.
| | |
|---|---|
| *G06K 9/00* | (2006.01) |
| *G06K 9/62* | (2006.01) |
| *G16C 20/70* | (2019.01) |
| *G16C 60/00* | (2019.01) |
| *G06N 20/00* | (2019.01) |
| *G16C 20/30* | (2019.01) |
| *G06N 5/00* | (2006.01) |

(52) U.S. Cl.
CPC ....... *G06K 9/00147* (2013.01); *G06K 9/6276* (2013.01); *G16C 20/70* (2019.02); *G16C 60/00* (2019.02); *G06N 5/003* (2013.01); *G06N 20/00* (2019.01); *G16C 20/30* (2019.02)

(58) Field of Classification Search
CPC combination set(s) only.
See application file for complete search history.

(56) References Cited

U.S. PATENT DOCUMENTS

| | | | |
|---|---|---|---|
| 6,882,739 B2 | 4/2005 | Kurtz et al. | |
| 7,680,557 B2 * | 3/2010 | Kim | G05B 19/41865 700/121 |
| 8,117,141 B1 | 2/2012 | Srinivasa et al. | |
| 8,835,895 B2 * | 9/2014 | Sumino | H01L 45/145 257/2 |
| 8,871,670 B2 * | 10/2014 | Seebauer | B82Y 30/00 502/300 |
| 8,932,347 B2 * | 1/2015 | Choubey | A61F 2/0077 424/423 |

(Continued)

OTHER PUBLICATIONS

Faken, et al., "Systematic analysis of local atomic structure combined with 3D computer graphics," Computational Materials Science, vol. 2, Issue 2, pp. 279-286 (Mar. 1994).

(Continued)

*Primary Examiner* — Michael B Holmes
(74) *Attorney, Agent, or Firm* — Foley & Lardner LLP

(57) ABSTRACT

A method of identifying grains in polycrystalline materials, the method including (a) identifying local crystal structure of the polycrystalline material based on neighbor coordination or pattern recognition machine learning, the local crystal structure including grains and grain boundaries, (b) pre-processing the grains and the grain boundaries using image processing techniques, (c) conducting grain identification using unsupervised machine learning; and (d) refining a resolution of the grain boundaries.

9 Claims, 5 Drawing Sheets

(56) References Cited

U.S. PATENT DOCUMENTS

| | | | |
|---|---|---|---|
| 9,175,174 B2* | 11/2015 | Kambe | B82Y 30/00 |
| 9,525,032 B2* | 12/2016 | Slack | C30B 23/00 |
| 9,683,682 B2* | 6/2017 | Narayanan | B23K 26/24 |
| 9,727,824 B2 | 8/2017 | Rose et al. | |
| 9,731,371 B2* | 8/2017 | Enyedy | B23K 9/1006 |
| 9,808,886 B2* | 11/2017 | Peters | B23K 15/0046 |
| 9,823,737 B2* | 11/2017 | Mazed | G10L 15/26 |
| 9,833,862 B2* | 12/2017 | Denney | B23K 26/14 |
| 9,839,978 B2* | 12/2017 | Narayanan | B23K 26/1423 |
| 9,914,765 B2* | 3/2018 | Timmer | C07K 14/765 |
| 9,937,580 B2* | 4/2018 | Peters | B23K 9/042 |
| 10,023,795 B2* | 7/2018 | Ning | C04B 35/6224 |
| 10,046,419 B2* | 8/2018 | Denney | B23K 26/1423 |
| 10,052,706 B2* | 8/2018 | Henry | B23K 9/092 |
| 10,052,707 B2* | 8/2018 | Henry | B23K 35/306 |
| 10,068,973 B2* | 9/2018 | Slack | H01L 21/2258 |
| 10,087,079 B2* | 10/2018 | Steiner, III | B82Y 30/00 |
| 10,419,655 B2* | 9/2019 | Sivan | H04W 4/80 |
| 10,529,003 B2* | 1/2020 | Mazed | G06Q 30/0639 |
| 10,584,916 B2 | 3/2020 | Gan | F25C 5/22 |
| 10,624,522 B1* | 4/2020 | Chan | A47L 15/4257 |
| 10,668,572 B2* | 6/2020 | Schaeffer | B23K 35/0261 |
| 10,682,721 B2* | 6/2020 | Narayanan | B23K 9/127 |
| 2015/0106035 A1 | 4/2015 | Vecchio et al. | |
| 2015/0199607 A1 | 7/2015 | Fang | |

OTHER PUBLICATIONS

Maras, et al., "Global transition path search for dislocation formation in Ge on Si(001)," Cornell University Library Materials Science, 29 pages (Jan. 25, 2016).

Abascal & Vega, "A general purpose model for the condensed phases of water: TIP4P/2005," Journal of Chemical Physics 123(23), 234505, 12 pages (2005).

Abascal, et al., "A potential model for the study of ices and amorphous water: TIP4P/Ice," Journal of Chemical Physics 122(23), 234511, 9 pages (2005).

Agarwal, et al., "Thermodynamic, Diffusional, and Structural Anomalies in Rigid-Body Water Models," Journal of Physical Chemistry B 115(21), pp. 6935-6945 (2011).

Berendsen, et al., "The missing term in effective pair potentials," Journal of Physical Chemistry 91(24), pp. 6269-6271 (1987).

Bigg & Hopwood, "Ice Nuclei in the Antarctic," Journal of the Atmospheric Sciences 20(3), pp. 185-188 (1963).

Blackford, "Sintering and microstructure of ice: a review," Journal of Physics D: Applied Physics 40(21), pp. R355-R385 (2007).

Chickos & Acree, "Enthalpies of Sublimation of Organic and Organometallic Compounds. 1910-2001," Journal of Physical and Chemical Reference Data 31(2), pp. 537-698 (2002).

Demott, et al., "Predicting global atmospheric ice nuclei distributions and their impacts on climate," Proceedings of the National Academy of Sciences 107(25), pp. 11217-11222 (2010).

Doran, et al., "Climate forcing and thermal feedback of residual lake-ice covers in the high Arctic," Limnology & Oceanography 41(5), pp. 839-848 (1996).

Durand, et al., "Deformation of grain boundaries in polar ice," Europhysics Letters 67(6), pp. 1038-1044 (2004).

Durham & Stern, "Rheological Properties of water Ice—Applications to Satellites of the Outer Planets," Annual Review of Earth and Planetary Sciences 29, pp. 295-330 (2001).

Ester, et al., "A density-based algorithm for discovering clusters a density-based algorithm for discovering clusters in large spatial databases with noise," Proceedings of the Second International Conference on Knowledge Discovery and Data Mining, pp. 226-231 (1996).

Faria, et al., "The microstructure of polar ice. Part I: Highlights from ice core research," Journal of Structural Geology 61, pp. 2-20 (2014).

Fisher & Koerner, "On the Special Rheological Properties of Ancient Microparticle-Laden Northern Hemisphere Ice as Derived from Bore-Hole and Core Measurements," Journal of Glaciology 32(112), pp. 501-510 (1986).

Gow, et al., "Physical and structural properties of the Greenland Ice Sheet Project 2 ice core: A review," Journal of Geophysical Research: Oceans 102(C12), pp. 26559-26575 (1997).

Grenfell, et al., "Reflection of solar radiation by the Antarctic snow surface at ultraviolet, visible, and near-infrared wavelengths," Journal of Geophysical Research: Atmospheres 99(D9), pp. 18669-18684 (1994).

Hadley & McCabe, "Coarse-grained molecular models of water: a review," Molecular Simulation 38(8-9), pp. 671-681 (2012).

Haji-Akbari & Debenedetti, "Direct calculation of ice homogeneous nucleation rate for a molecular model of water," Proceedings of the National Academy of Sciences 112(34), pp. 10582-10588 (2015).

Handel, et al., "Direct Calculation of Solid-Liquid Interfacial Free Energy for Molecular Systems: TIP4P Ice-Water Interface," Physical Review Letters 100, 036104, 4 ppages (2008).

Holz, et al., "Temperature-dependent self-diffusion coefficients of water and six selected molecular liquids for calibration in accurate 1H NMR PFG measurements," Physical Chemistry Chemical Physics 2(20), pp. 4740-4742 (2000).

Horn, et al., "Development of an improved four-site water model for biomolecular simulations: TIP4P-Ew," Journal of Chemical Physics 120(20), pp. 9665-9678 (2004).

Jorgensen, et al., "Comparison of simple potential functions for simulating liquid water," Journal of Chemical Physics 79, pp. 926-935 (1983).

Kokhanovsky, et al., "Reflective properties of natural snow: approximate asymptotic theory versus in situ measurements," IEEE Transactions on Geoscience and Remote Sensing 43(7), pp. 1529-1535 (2005).

Lee, "Temperature Dependence on Structure and Self-Diffusion of Water: A Molecular Dynamics Simulation Study using SPC/E Model," Bulletin of the Korean Chemical Society 34(12), pp. 3800-3804 (2013).

Li, et al., "Freeze casting of porous materials: review of critical factors in microstructure evolution," International Materials Review 57(1), pp. 37-60 (2013).

Liu, et al., "Direct Measurement of Critical Nucleus Size in Confined Volumes," Langmuir 23(13), pp. 7286-7292 (2007).

Mahoney & Jorgensen, "A five-site model for liquid water and the reproduction of the density anomaly by rigid, nonpolarizable potential functions," Journal of Chemical Physics 112(20), pp. 8910-8922 (2000).

Majewski, et al., "Toward a Determination of the Critical Size of Ice Nuclei. A Demonstration by Grazing Incidence X-ray Diffraction of Epitaxial Growth of Ice under the C31H63OH Alcohol Monolayer," Journal of Physical Chemistry 98(15), pp. 4087-4093 (1994).

Malkin, et al., "Structure of ice crystallized from supercooled water," Proceedings of the National Academy of Sciences 109(4), pp. 1041-1045 (2012).

Mangold, et al., "Experimental and theoretical deformation of ice-rock mixtures: Implications on rheology and ice content of Martian permafrost," Planetary and Space Science 50(4), pp. 385-401 (2002).

Molinero & Moore, "Water Modeled As an Intermediate Element between Carbon and Silicon," The Journal of Physical Chemistry B 113(13), pp. 4008-4016 (2009).

Montagnant & Duval, "The viscoplastic behaviour of ice in polar ice sheets: experimental results and modelling," Comptes Rendus Physique 5(7), pp. 699-708 (2004).

Montagnat & Duval, "Rate controlling processes in the creep of polar ice, influence of grain boundary migration associated with recrystallization," Earth and Planetary Science Letters 183(1-2), pp. 179-186 (2000).

Montagnat, et al., "Lattice distortion in ice crystals from the Vostok core (Antarctica) revealed by hard X-ray diffraction; implication in the deformation of ice at low stresses," Earth and Planetary Science Letters 214(1-2), pp. 369-378 (2003).

Moore & Molinero, "Is it cubic? Ice crystallization from deeply supercooled water," Physical Chemistry Chemical Physics 13(44), pp. 20008-20016 (2011).

Nelder & Mead, "A Simplex Method for Function Minimization," The Computer Journal 7(4), pp. 308-313 (1965).

(56) References Cited

OTHER PUBLICATIONS

Orsi, et al., "Comparative assessment of the ELBA coarse-grained model for water," Molecular Physics 112(11), pp. 1566-1576 (2014).
Perovich & Elder, "Temporal evolution of Arctic sea-ice temperature," Annals of Glaciology 33, pp. 207-211 (2001).
Perovich, et al., "Variability in Arctic sea ice optical properties," Journal of Geophysical Research: Oceans 103(C1), pp. 1193-1208 (1998).
Petrovic, "Review Mechanical properties of ice and snow," Journal of Materials Science 38(1), pp. 1-6 (2003).
Pi, et al., "Anomalies in water as obtained from computer simulations of the TIP4P/2005 model: density maxima, and density, isothermal compressibility and heat capacity minima," Molecular Physics 107(46), pp. 365-374 (2009).
Plimpton, "Fast Parallel Algorithms for Short-Range Molecular Dynamics," Journal of Computational Physics 117(1), pp. 1-19 (1995).
Skinner, et al., "The structure of water around the compressibility minimum," Journal of Chemical Physics 141, 214507, 7 pages (2014).
Soper, "The Radial Distribution Functions of Water as Derived from Radiation Total Scattering Experiments: Is There Anything We Can Say for Sure?," ISRN Physical Chemistry, 279463, 67 pages (2013).
Sosso, et al., "crystal Nucleation in Liquids: Open Questions and Future Challenges in Molecular Dynamics Simulations," Chemical Reviews 116(12), pp. 7078-7116 (2016).
Ushio, "Factors affecting fast-ice break-up frequency in Lutzow-Holm Bay, Antarctica," Annals of Glaciology 44, pp. 177-182 (2006).
Vega & Abascal, "Relation between the melting temperature and the 406 temperature of maximum density for the most common models of water," Journal of Chemical Physics 123(14), 144504, 8 pages (2005).
Vega, et al., "What ice can teach us about water interactions: a critical comparison of the performance of different water models," Faraday Discussions 141, pp. 251-276 (2009).
Warren, "Optical properties of snow," Reviews of Geophysics 20(1), pp. 67-89 (1982).
Weeks & Lee, "Observations on the Physical Properties of Sea-Ice at Hopedale, Labrador," ARCTIC 11(3), pp. 134-155 (1958).
Weikusat, et al., "Subgrain boundaries and related microstructural features in EDML (Antarctica) deep ice core," Journal of Geology 55(191), pp. 461-472 (2009).
Wellner, et al., "Distribution of glacial geomorphic features on the Antarctic continental shelf and correlation with substrate: implications for ice behavior," Journal of Glaciology 47(158), pp. 397-411 (2001).
Worby, et al., "East Antarctic Sea Ice: A Review of Its Structure, Properties and Drift," Antarctic Sea Ice: Physical Processes, Interactions and Variability 74, pp. 41-67 (1998).
Yen, "Review of Thermal Properties of Snow, Ice and Sea Ice," CRREL Report 81-10, 37 pages (1981).
Abascal & Vega, "A general purpose model for the condensed phases of water: TIP4P/2005," The Journal of Chemical Physics 123, 234505, 12 pages (2005).
Agarwal, et al., "Thermodynamic, Diffusional, and Structural Anomalies in Rigid-Body Water Models," The Journal of Physical Chemistry C 115(21), pp. 6935-6945 (2011).
Amaya, et al., "How Cubic Can Ice Be?," The Journal of Physical Chemistry Letters 8(14), pp. 3216-3222 (2017).
Chickos & Acree, "Enthalpies of Sublimation of Organic and Organometallic Compounds. 1910-2001," Journal of Physical and Chemical Reference Data 31, 537 (2002).
Durham, et al., "Effects of dispersed particulates on the rheology of water ice at planetary conditions," Journal of Geophysical Research: Planets 97(E12), pp. 20883-20897 (1992).
Engel, et al., "Anharmonic Nuclear Motion and the Relative Stability of Hexagonal and Cubic ice," Physical Review X 5, 021033, 10 pages (2015).

Espinosa, et al., "Ice-Water Interfacial Free Energy for the TIP4P, TIP4P/2005, TIP4P/Ice, and mW Models As Obtained from the Mold Integration Technique," The Journal of Physical Chemistry C 120(15), pp. 8068-8075 (2016).
Espinosa, et al., "The mold integration method for the calculation of the crystal-fluid interfacial free energy from simulations," The Journal of Chemical Physics 141, 134709, 16 pages (2014).
Ester, et al., "A Density-Based Algorithm for Discovering Clusters in Large Spatial Databases with Noise," Proceedings of the Second International Conference on Knowledge Discovery and Data Mining, pp. 226-231 (1996).
Gow & Williamson, "Rheological implications of the internal structure and crystal fabrics of the West Antarctic ice sheet as revealed by deep core drilling at Byrd Station," Geological Society of America Bulletin 87(12), pp. 1665-1677 (1976).
Hansen, et al., "Modelling Ice Ic of Different Origin and Stacking-Faulted Hexagonal Ice Using Neutron Powder Diffraction Data," Physics and Chemistry of Ice: Proceedings of the 11th International Conference, pp. 201-208 (2007).
Henkelman & Jonsson, "Improved tangent estimate in the nudged elastic band method for finding minimum energy paths and saddle points," The Journal of Chemical Physics 113, pp. 9978-9985 (2000).
Henkelman, et al., "A climbing image nudged elastic band method for finding saddle points and minimum energy paths," The Journal of Chemical Physics 113, pp. 9901-9940 (2000).
Hondoh, "Dislocation mechanism for transformation between cubic ice Ic and hexagonal ice Ih," Philosophical Magazine 95(32), pp. 3590-3620 (2015).
Hondoh, et al., "Formation and annihilation of stacking faults in pure ice," The Journal of Physical Chemistry 87(21), pp. 4040-4044 (1983).
Jacobson, et al., "How Short Is Too Short for the Interactions of a Water Potential? Exploring the Parameter Space of a Coarse-Grained Water Model Using Uncertainty Quantification," The Journal of Physical Chemistry B 118(28), pp. 8190-8202 (2014).
Johnston & Molinero, "Crystallization, Melting, and Structure of Water Nanoparticles at Atmospherically Relevant Temperatures," Journal of the American Chemical Society 134(15), pp. 6650-6659 (2012).
Jorgensen & Tirado-Rives, "Potential energy functions for atomic-level simulations of water and organic and biomolecular systems," Proceedings of the National Academy of Sciences 102(19), pp. 6665-6670 (2005).
Kuhs, et al., "Extent and relevance of stacking disorder in 'ice Ic'," Proceedings of the National Academy of Sciences 109(52), pp. 21259-21264 (2012).
Kuo, et al., "Liquid Water from First Principles: Investigation of Different Sampling Approaches," The Journal of Physical Chemistry B 108(34), pp. 12990-12998 (2004).
Lu, et al., "Coarse-Graining of TIP4P/2005, TIP4P-Ew, SPC/E, and TIP3P to Monatomic Anisotropic Water Models Using Relative Entropy Minimization," Journal of Chemical Theory and Computation 10(9), pp. 4104-4120 (2014).
Mahoney & Jorgensen, "A five-site model for liquid water and the reproduction of the density anomaly by rigid, nonpolarizable potential functions," The Journal of Chemical Physics 112, pp. 8910-8922 (2000).
Malkin, et al., "Stacking disorder in ice I," Physical Chemistry Chemical Physics 17(1), pp. 60-76 (2015).
Maras, et al., "Global transition path search for dislocation formation in Ge on Si(001)," Computer Physics Communications 205, pp. 13-21 (2016).
Marrone & Car, "Nuclear Quantum Effects in Water," Physical Review Letters 101, 017801, 4 pages (2008).
Nakano, "A space-time-ensemble parallel nudged elastic band algorithm for molecular kinetics simulation," Computer Physics Communications 178(4), pp. 280-289 (2008).
Reddy, et al., "On the accuracy of the MB-pol many-body potential for water: interaction energies, vibrational frequencies, and classical thermodynamic and dynamical properties from clusters to liquid water and ice," The Journal of Chemical Physics 145, 194504, 37 pages (2016).

(56) References Cited

OTHER PUBLICATIONS

Ren & Ponder, "Polarizable Atomic Multipole Water Model for Molecular Mechanics Simulation," The Journal of Physical Chemistry B 107(24), pp. 5933-5947 (2003).

Schiotz, et al., "Softening of nanocrystalline metals at very small grain sizes," Nature 391, pp. 561-563 (1998).

Shilling, et al., "Measurements of the vapor pressure of cubic ice and their implications for atmospheric ice clouds," Geophysical Research Letters 33(17), L17801, 5 pages (2006).

Skinner, et al., "The structure of water around the compressibility minimum," The Journal of Chemical Physics 141, 214507, 7 pages (2014).

Soper, "The Radial Distribution Functions of Water as Derived from Radiation Total Scattering Experiments: Is There Anything We Can Say for Sure?," International Scholarly Research Notices: Physical Chemistry 2013, 279463, 67 pages (2013).

Stuart, et al., "A reactive potential for hydrocarbons with intermolecular interactions," The Journal of Chemical Physics 112, pp. 6472-6486 (2000).

Stukowski, "Visualization and analysis of atomistic simulation data with OVITO—the Open Visualization Tool," Modelling and Simulation in Materials Science and Engineering 18, 015012, 7 pages (2010).

Togo & Tanaka, "First principles phonon calculations in materials science," Scripta Materlialia 108, pp. 1-5 (2015).

Vega & Abascal, "Relation between the melting temperature and the temperature of maximum density for the most common models of water," The Journal of Chemical Physics 123, 144504, 8 pages (2005).

Vega & Abascal, "Simulating water with rigid non-polarizable models: a general perspective," Physical Chemistry Chemical Physics 13(44), pp. 19663-19688 (2011).

Vega, et al., "The melting temperature of the most common models of water," The Journal of Chemical Physics 122, 114507, 9 pages (2005).

Wang, et al., "Systematic Improvement of a Classical Molecular Model of Water," The Journal of Physical Chemistry B 117(34), pp. 9956-9972 (2013).

Boulton & Hindmarsh, "Sediment deformation beneath glaciers: Rheology and geological consequences," Journal of Geophysical Research: Solid Earth 92(B9), pp. 9059-9082 (1987).

Darre, et al., "Coarse-grained models of water," WIREs Computational Molecular Science 2(6), pp. 921-930 (2012).

Ghormley, "Enthalpy Changes and Heat-Capacity Changes in the Transformations from High-Surface-Area Amorphous Ice to Stable Hexagonal Ice," The Journal of Chemical Physics 48, pp. 503-508 (1968).

Gillen, et al., "Self-Diffusion in Liquid Water to −31 C," Journal of Chemical Physics 57(12), pp. 5117-5119 (1972).

Hudait, et al., "Free energy contributions and structural characterization of stacking disordered ices," Physical Chemistry Chemical Physics 18(14), pp. 9544-9553 (2016).

Ketcham & Hobbs, "An experimental determination of the surface energies of ice," The Philosophical Magazine: a Journal of Theoretical Experimental and Applied Physics 19(162), pp. 1161-1173 (1969).

McMillan & Los, "Vitreous Ice: Irreversible Transformations During Warm-Up," Nature 206, pp. 806-807 (1965).

Moore & Molinero, "Ice crystallization in water's 'no-man's land'," Journal of Chemical Physics 132, 244504 (2010).

Murray, et al., "The formation of cubic ice under conditions relevant to Earth's atmosphere," Nature 434, pp. 202-205 (2005).

Nada & Van Der Eerden, "An intermolecular potential model for the simulation of ice and water near the melting point: A six-site model of H2O," Journal of Chemical Physics 118(16), pp. 7401-7413 (2003).

Narten, et al., "Diffraction pattern and structure of amorphous solid water at 10 and 77 K," Journal of Chemical Physics 64, pp. 1106-1121 (1976).

Tersoff, "New empirical approach for the structure and energy of covalent systems," Physical Review B 37, pp. 6991-7000 (1988).

* cited by examiner

For atomic data,  For experimental data,

MACHINE LEARNING TECHNIQUE TO IDENTIFY GRAINS IN POLYCRYSTALLINE MATERIALS SAMPLES

STATEMENT OF GOVERNMENT INTEREST

The United States Government claims certain rights in this invention pursuant to Contract No. DE-AC02-06CH11357 between the U.S. Department of Energy and UChicago Argonne, LLC, as operator of Argonne National Laboratories.

FIELD OF THE INVENTION

The present invention relates generally to the field of machine learning techniques for identifying grains in polycrystalline materials samples.

BACKGROUND

This section is intended to provide a background or context to the invention recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

Properties of polycrystalline materials (mechanical, electrical, magnetic, optical, etc.) depend on the characteristics of grain boundaries and distribution of grain sizes. Various experimental and theoretical methods may be used to study polycrystalline materials at different scales; however, grain analysis necessitates a real-time and accurate way of identifying grains. Currently available grain size analysis technologies are constructed on two-dimensional (2-D) microstructural images such as the line intercept method (ASTM standard) or techniques which implement ImageJ or SIMA-GIS software. However, these techniques cannot be extended to three-dimensional (3-D) data sets. A fundamental understanding of polycrystalline materials are needed for technological and energy applications using grain analysis techniques which include 3-D data sets.

Thus, a need exists for improved technology, including development of machine learning techniques for identifying grains in polycrystalline materials samples.

SUMMARY

One embodiment of the invention relates to a method of identifying grains in polycrystalline materials. The method includes (a) identifying local crystal structure of the polycrystalline material based on neighbor coordination or pattern recognition machine learning, the local crystal structure comprising grains and grain boundaries, (b) pre-processing the grains and the grain boundaries using image processing techniques, (c) conducting grain identification using unsupervised machine learning, and (d) refining a resolution of the grain boundaries.

In one embodiment, the step of identifying local crystal structure is based on neighbor coordination and comprises identifying the atomic structure of a first neighbor of the grains and grain boundaries as at least one of hexagonal close packing (hcp), face-centered cubic (fcc), body-centered cubic (bcc), and icosahedral. In one embodiment, the step of identifying local crystal structure further comprises identifying the atomic structure of a second neighbor of the grains and grain boundaries as at least one of hexagonal close packing (hcp), face-centered cubic (fcc), body-centered cubic (bcc), and icosahedral.

In one embodiment, the step of identifying local crystal structure generates voxels and a number count of (a) each type of atomic structure for the first neighbor, and (b) each type of atomic structure for the second neighbor. In one embodiment, the step of identifying local crystal structure is based on unsupervised machine learning. In one embodiment, the step of pre-processing comprises applying a uniform filter to the voxels to reduce noise within the grains and improve contrast of the grain boundaries. In one embodiment, the method further comprises labeling the voxels as either in the grain or at the grain boundary. In one embodiment, the step of conducting grain identification comprises segregating individual grains by classifying the voxels based on grain index and assigning the voxels to be a portion of the grain. In one embodiment, the step of refining the grains comprises reassigning voxels labeled as at the boundary to its spatially nearest grain.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The disclosure will become more fully understood from the following detailed description, taken in conjunction with the accompanying figures, in which:

FIG. 1A shows the total potential energy variation of the 2 million-water molecule system during the cooling phase from 275K to 210.5K and at longer times when the system temperature is kept constant at 210.5K. Four distinct stages are identified (i) initial quiescent time when no nucleation event occurs, (ii) nucleation followed by an initial slow transformation shown by the slow energy decreasing period, (iii) a fast transformation phase of the grains shown by the rapid decrease in potential energy, and (iv) a plateauing of potential energy marks the completion of the phase transformation. FIG. 1B shows snapshots of subcritical water nuclei during the long quiescent phase leading up to the nucleation. The first nucleation event for the 2 million-water system occurs at t=258 ns. Liquid water molecules are not shown for clarity. FIG. 1C illustrates molecular dynamic simulation snapshots of the various stages of grain growth and grain boundary during the post-nucleation stage. Liquid water is omitted for clarity. FIG. 1D shows the temporal evolution of the number of subcritical water nuclei (size<100 molecules) from the quiescent period and the initial appearance of stable nuclei during the post-nucleation stage. FIG. 1E shows the corresponding temporal evolution of the fraction of cubic and hexagonal ice.

FIG. 2A shows a temporal evolution of the number of grains in polycrystalline ice during annealing at 260K. Initially, an Ostwald ripening stage is observed illustrating a sharp drop in the number of grains at t<10 ns due to rapid dissolution of smaller sized grains into amorphous ice. After the Ostwald ripening stage, a slower grain consolidation phase is observed due to grain boundary migration. Finally, a stable phase is observed where the number of grains remains unchanged. The inset shows the corresponding temporal evolution of the grain size. FIG. 2B shows the fractional change in amorphous and crystalline ice during the grain dissolution phase. The maxima and minima in the amorphous and crystalline population, respectively, result from the relative kinetics of grain dissolution and grain growth. FIG. 2C shows snapshots from the multi-million MD trajectory of the rapid dissolution of smaller sized grains into amorphous ice while the larger, energetically stable grains survive and grow by consuming the amorphous ice. The amorphous ice is not shown for clarity. The panel below depicts the bar graph of grain size distribution at the time instant corresponding to the snapshot. Initially, at t=399 ns, there is a large population of smaller sized grains. With time, the population of smaller-sized grains progressively decreases while the population of larger-sized grains increases. FIG. 2C shows a zoomed-in view of snapshots from the multi-million MD trajectories showing the grain growth via the classic grain boundary migration. Larger grains are shown to grow at the expense of smaller grains. The grain size distribution shows the associated progression towards larger-sized grains as a result of grain boundary migration.

In FIG. 3A, hexagonal (Ih), cubic (Ic), and amorphous/liquid phases of ice are determined using a 2nd neighbor structure identification algorithm. FIG. 3B shows pre-processing of the grains and grain boundaries using image processing techniques. FIG. 3C shows grain identification using unsupervised machine learning.

DETAILED DESCRIPTION

Figure 1A:
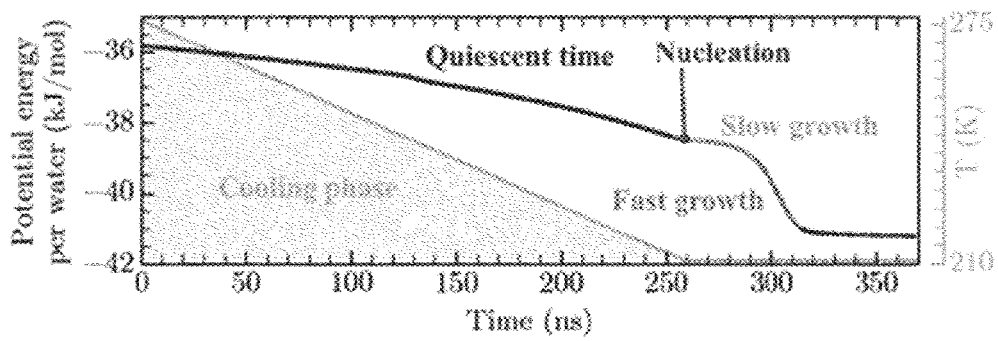
FIGS. 1A-1E depict system dynamics and evolution of structural motifs during the cooling phase from homogeneous nucleation to grain boundary formation and grain growth. Specifically.

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Growth of polycrystalline grains of ice from deeply supercooled water to larger crystallites is a common natural phenomena and utilized across many applications, such as cryopreservation of food and biological samples. Typically, grain sizes of most commonly observed forms of ice range from the millimeter to centimeter range. As in most polycrystalline materials, grain size may impact the mechanical, physical, thermal and optical properties of a material. However, growth mechanisms describing grain formation are often complex and include several competing factors, such as different nucleating ice phases, transport phenomena and microstructural evolution coupled with defect and solvation dynamics. As such, little is known about the origins and sequencing steps from nucleation to ice grain formation and growth.

Despite exponential growth in computing resources and availability of different theoretical water models, an accurate and computationally efficient molecular level description of mesoscopic grain growth remains a challenge. The underlying phase transitions and dynamical processes in deeply supercooled systems are often inaccessible due to limitations imposed by system sizes, timescales, and their sluggish kinetics.

Numerous atomistic and coarse-grained (CG) models have attempted to describe the thermodynamic properties and dynamical behavior of water with varying degrees of success in sacrificing either predictive power or computational cost/efficiency. Currently available CG models are a viable alternative with several orders of magnitude improvements in computational efficiency, allowing million-atom simulations to effortlessly reach microsecond time scales. However, while such improvements in computational efficiency are needed for mechanistic understanding grain formation and growth, CG models have often lacked sufficient predictive functionality to provide a complete solution. Capturing physical and thermodynamic properties of water such as density anomaly, melting transition and relative density difference between ice and liquid water, remains a challenge for current predictive technologies.

Computational Bond Order Potential Modeling

In the present disclosure, a machine-learnt coarse-grained bond order potential (BOP) model is used that outperforms existing models in describing the structure, thermodynamic and transport properties of both ice and liquid water. The disclosed BOP model significantly improves computational efficiency and is at least two to three orders of magnitude cheaper compared with currently existing atomistic models. Supervised machine learning used to develop BOP model and unsupervised machine learning using BOP model performed for grain identification.

The present BOP model treats each water molecule as one bead, with a potential form capable of describing tetrahedral solids. The Tersoff-Brenner formalism, based on Pauling bond order concept, is used to describe the short-range directional interactions between CG water beads. The potential energy V of the system is given by a summation of pair interactions, which is expressed as:

$$V = \frac{1}{2} \sum_i \sum_{j \neq i} f_C(r_{ij})[f_R(r_{ij}) + b_{ij} f_A(r_{ij})]$$

where $f_C(r_{ij})$, $f_R(r_{ij})$, and $f_A(r_{ij})$ are the cutoff, repulsive, and attractive pair interactions, respectively, between bead i and j separated by a distance $r_{ij}$, and $b_{ij}$ is a bond-order parameter which modifies the pair interaction strength between bead i and j depending on their local chemical environment.

The cutoff function limits the range of interaction mainly to improve computational efficiency. The function is given by:

$$f_C(r) = \begin{cases} 1, & r < R - D \\ \frac{1}{2} - \frac{1}{2}\sin\left(\frac{\pi(r-R)}{2D}\right), & R - D < r < R + D \\ 0, & r > R + D \end{cases}$$

where R and D are free parameters that are chosen as to include only the first nearest neighbors, such that their pair interactions are smoothly reduced starting from the distance R−D and are completely turn off beyond the distance R+D.

The repulsive and attractive pair interactions between CG water beads are modeled using exponential decay functions given by:

$$f_R(r) = A e^{-\lambda_1 r}$$

$$f_A(r) = -B e^{-\lambda_2 r}$$

where A, B, $\lambda_1$, and $\lambda_2$ are free parameters that control the overall strength and length scale of the repulsive and attractive potentials. Furthermore, the strength of $f_A(r)$ is scaled by a bond-order term $b_{ij}$ which is given by:

$$b_{ij} = (1 + \beta^n \xi_{ij}^n)^{-\frac{1}{2n}}$$

$$\xi_{ij} = \sum_{k \neq ij} f_C(r_{ik}) g(\theta_{ijk})$$

$$g(\theta) = 1 + \frac{c^2}{d^2} - \frac{c^2}{[d^2 + (\cos\theta - \cos\theta_0)^2]}$$

where $\beta$, n, c, d, and $\cos\theta_0$ are free parameters. $\zeta_{ij}$ defines the effective coordination of bead i, taking into account the number of its neighboring beads and their relative distances $r_{ik}$ and angles $\theta_{ijk}$. The three-body angular dependence is described by the function $g(\theta)$, which has a minimum defined by $\cos\theta_0$ and the strength and sharpness of its effect is controlled by c and d.

Water molecules are modeled using a 1:1 coarse-grained (CG) model. The CG mapping of atomistic water molecules into CG water beads is conducted by removing hydrogen atoms, such that the CG beads are placed at the oxygen atom positions. Representing water molecules as monoatomic beads and using a BOP model leads to a more significant speed-up in molecular dynamic (MD) simulations than by a factor of three because of a reduced number of atoms. This is because larger simulation time steps (10 femtoseconds vs 1 femtosecond) are possible since there are no fast O—H vibrations, there is a significantly reduced number of pairwise interactions due to the reduced number of atoms, and the BOP potential form has reduced complexity. One-to-one CG mapping of water provides a balance between model simplicity and computational efficiency.

Cooling Phase from Homogeneous Nucleation to Grain Boundary Formation and Grain Growth A molecular dynamic simulation was performed on multimillion water molecules using the BOP model to understand the molecular level sequence of steps required for growth of homogeneous nucleation of supercooled water to the formation and growth of grains of ice. FIGS. 1A to 1E summarize the initial stages of formation of polycrystalline ice for when water is slowly cooled from 275K to 210.5K over 258 ns (cooling rate ~2.5×10⁸ K/s). Following the appearance of the first stable nuclei at ~210.5K, the temperature was held at 210.5K for an additional 110 ns to study nucleation and growth processes in this homogeneously nucleated water.

FIG. 1A shows potential energy variation as a function of time during the cooling phase and constant temperature phase. Four distinct stages were identified during the freezing process (a) a long quiescent time period of about 250 nanoseconds before the first nucleation events, (b) a period of slow transformation with a limited number of nuclei (eight at t=270 ns), (c) an accelerated transformation driven by growth of a greater number of nuclei (about 80 at 300 ns), and (d) completion of grain growth to form a polycrystalline box of ice.

Figure 1B:
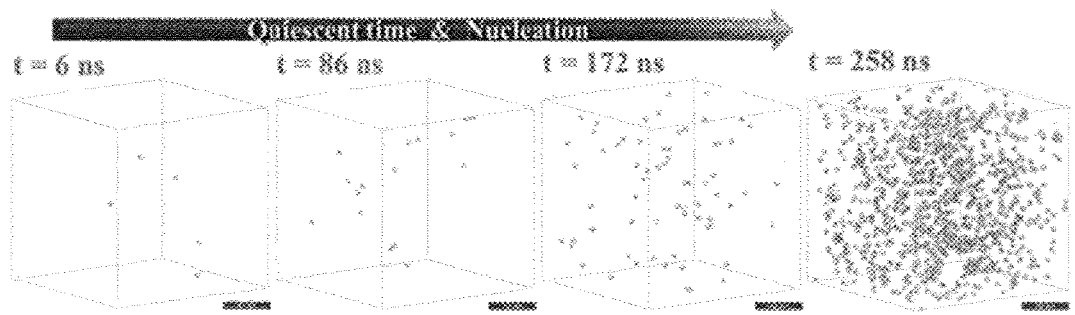
Figure 1C:
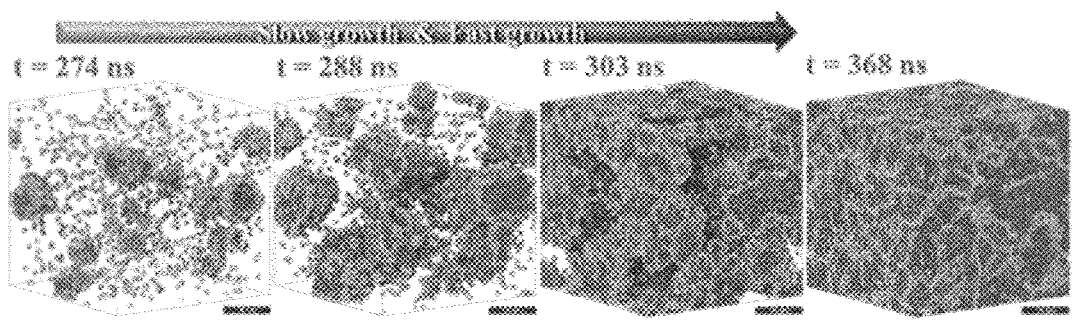
Figure 1D:
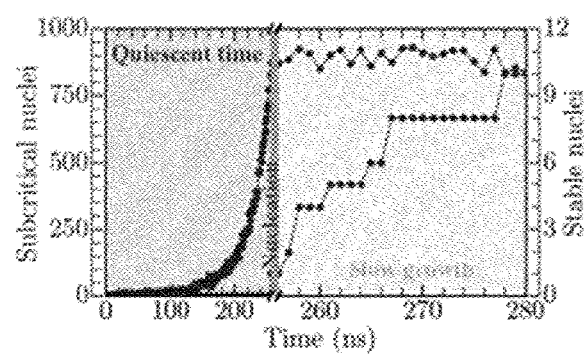

FIG. 1B shows corresponding snapshots during the initial quiescent period when the system explores the relatively flat energy landscape before entering the nucleation and growth period. This molecular level illustration is consistent with classical nucleation theory; the quiescent period is marked by pronounced fluctuation of many subcritical nuclei which rapidly form, break and reform in the supercooled liquid as shown in FIG. 1D. The post-quiescent period shown by MD snapshots in FIG. 1C is marked by formation of multiple stable nuclei which grow slowly, followed by a rapid growth phase when the grains begin to percolate through the entire three-dimensional space. The completion of the growth phase is characterized by formation of a polycrystalline ice with the nanoscopic grains separated by boundaries comprising amorphous ice. A local structure analysis of the growing structure reveals that the grains are comprised of stacking disordered ice (ISD), i.e. randomly mixed alternating sheets of hexagonal and cubic ice (FIG. 1C). The evolution, extent and relevance of stacking disorder in polycrystalline ice may be explained by the MD simulations, which unambiguously capture the competition between cubic (Ic) and hexagonal (Ih) phases leading to the formation of ISD at atmospheric conditions.

Figure 1E:
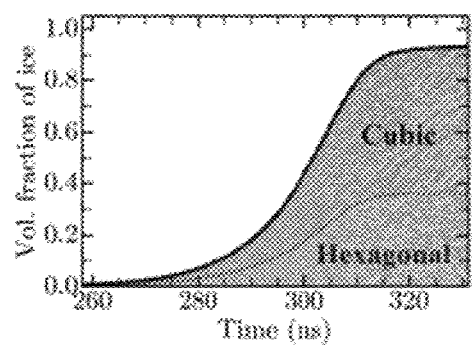

FIG. 1E shows the evolving ice structure becomes increasingly rich in Ic, as compared to the more stable Ih phase; the ratio of cubic to hexagonal is approximately 1.6 at the conclusion of t=350 ns. The observed preference for cubic ice formation is consistent with multiple experimental results.

The microstructure obtained at the conclusion of the cooling and constant temperature simulation (FIG. 1C) is fine grained (average grain size is approximately 15,000 water molecules). This fine microstructure is annealed over a time span ranging from a microsecond to several seconds to naturally observed grain sizes ranging from micro-meters to millimeters. An atomistic picture of the post-nucleation coarsening of grains has remained largely elusive. To study the molecular rearrangement processes driving the transformation to large grain sizes, the nanocrystalline sample (which was obtained from quenching and holding at 210K) was annealed at approximately 260K (a typical temperature attained by glaciers due to seasonal variations).

Mechanisms Grain Boundary Formation and Grain Growth

Figure 2A:
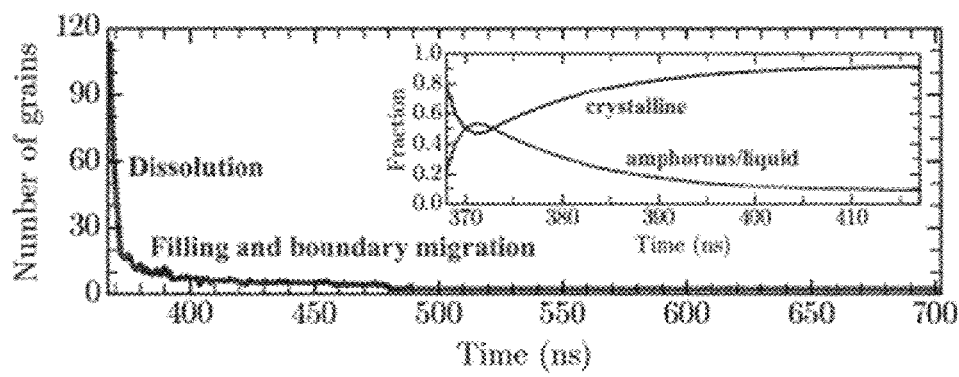
FIGS. 2A-2C depict mechanisms of formation of grain boundaries and grain growth in ice nucleated from supercooled water. Specifically.
Figure 2B:
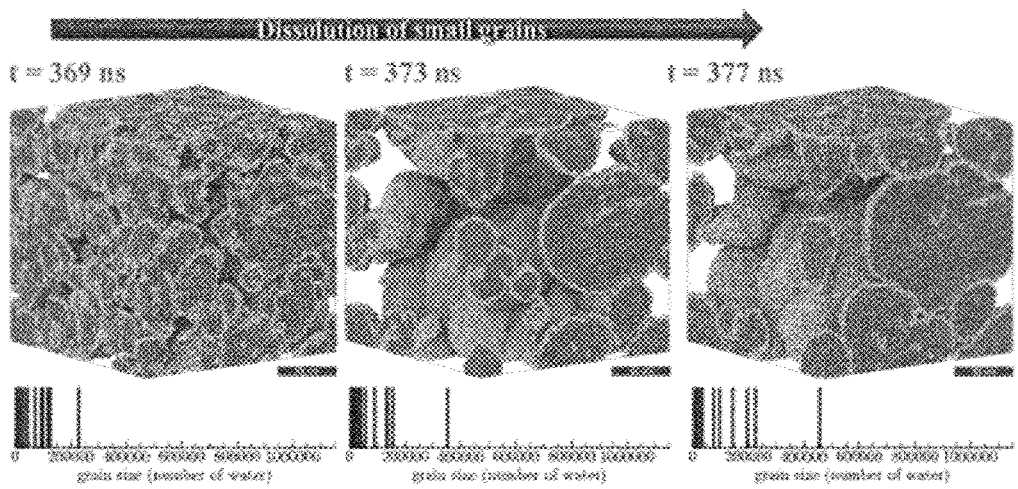
Figure 2C:
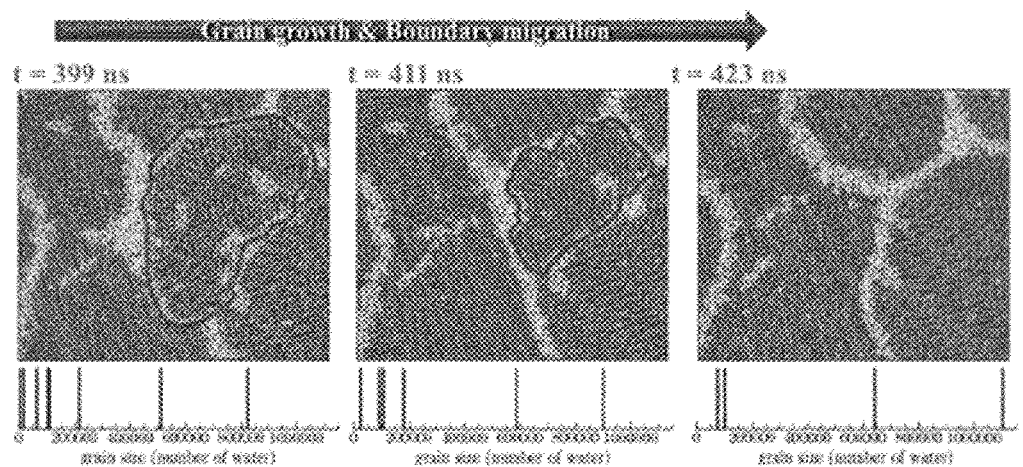

Two mechanisms drive the annealing of ice crystallites. Initially, concurrent dissolution of small grains (grain size<2000 water molecules) and growth of large grains (grain size>11,000 water molecules) are observed analogous to the Ostwald ripening process in solution. Within about 10 ns of annealing (i.e. t=about 368 to about 378 ns, FIG. 2A) the small grains, owing to their low stability (characterized as a high surface to volume ratio), melt away; the water molecules from this melt subsequently impinge, and contribute to the growth of nearby larger grains (FIG. 2B). The interplay between melting and grain growth leads to maxima and minima at about t=371 ns in the fraction of amorphous and crystalline phases, respectively. Larger grains continue to grow into space vacated by the dissolved grains, and occupy the entire volume of the box (within the time range of t=378 ns to 430 ns). A second stage of slower growth is initiated (at time t=430 ns and beyond) where grain coarsening continues through boundary migration until only two grains remain in the box. FIG. 2C shows the grain boundary migration mechanism. The images show consumption of a grain by its neighbors over a period of ~30 ns. Bar graphs below each frame (i.e. t=399 ns, t=411 ns, and t=423 ns) show grain size distribution over the entire simulation cell and reveal the progression to larger grain sizes.

Machine Learning Analysis of Grain Size Distribution

Figure 3A:
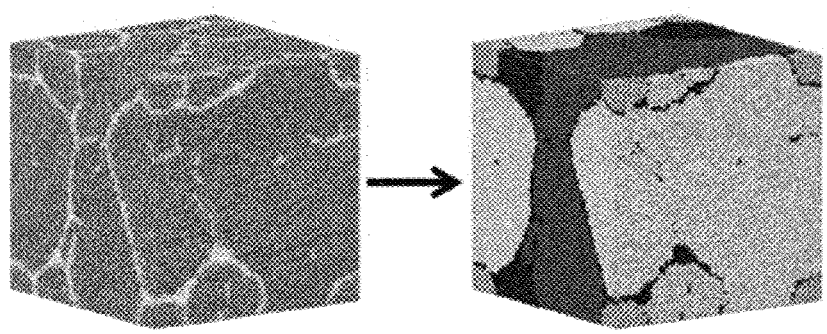
FIGS. 3A-3C depict machine learning analysis of grain size distribution in ice.
Figure 3B:
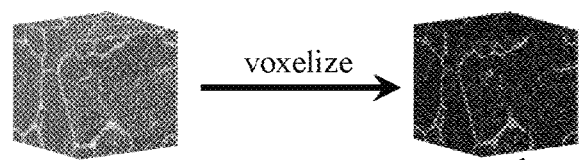
Figure 3B:
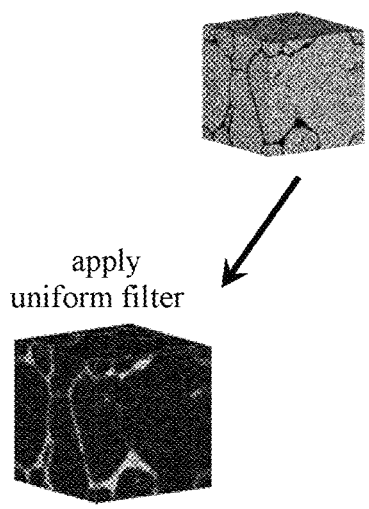
Figure 3B:
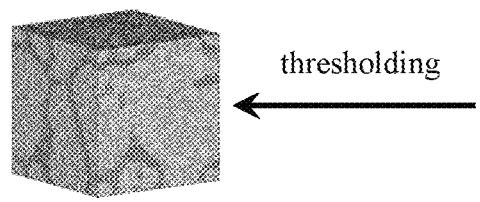
Figure 3C:
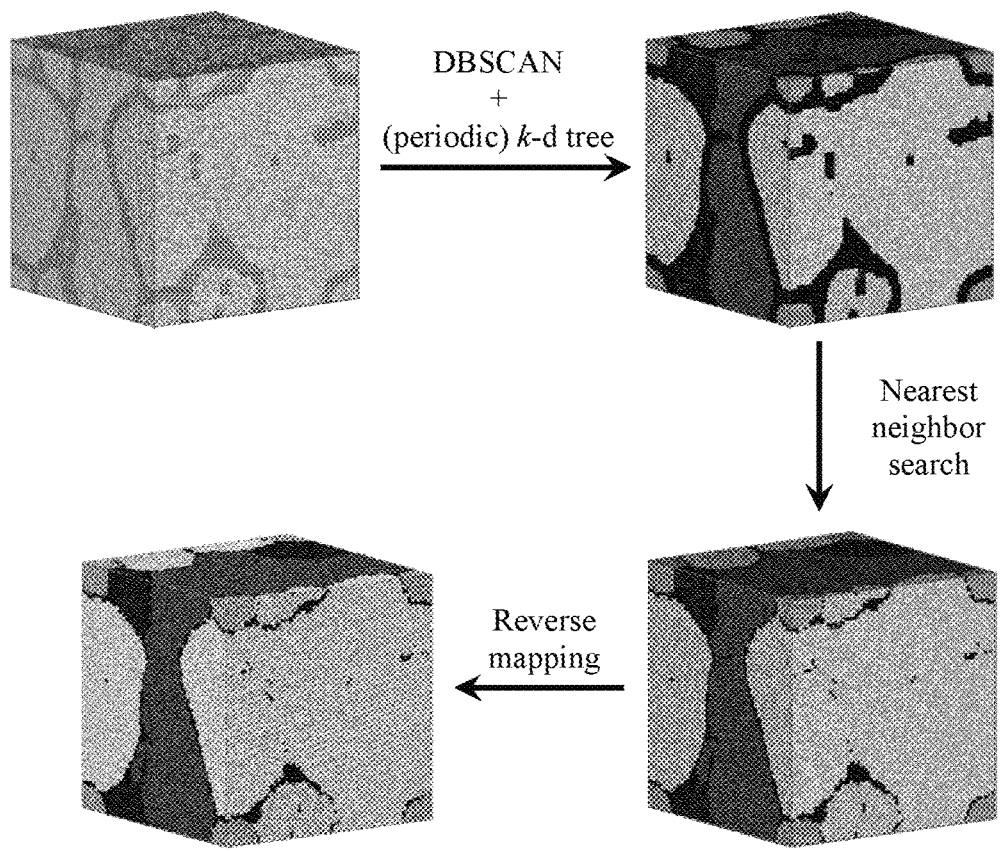

As explained above, currently available grain size analysis technologies are constructed on 2-D data sets which cannot be extended to 3-D data sets. FIGS. 3A-3C depict machine learning analysis of grain size distribution in ice according to one embodiment of the present disclosure.

While ice is one material upon which the grain size analysis techniques of the present disclosure may be applied, other polycrystalline materials, such as metals, ceramics, semiconductors, etc. may also be used for 3-D grain size analysis determinations. In FIG. 3A, hexagonal (Ih), cubic (Ic), and amorphous/liquid phases of ice are determined using a 2nd neighbor structure identification (extended common neighbor) algorithm implemented in the program OVITO. The number of grains and their individual sizes are estimated using a 3-D grain identification procedure which is based on image processing techniques and unsupervised machine learning principles.

FIG. 3B shows pre-processing of the grains and grain boundaries using 3-D image processing techniques. Voxels are created and filled with values equal to the number count of ice Ih and Ic bead types to handle the stacking disordered structure in ice. The procedure first generates voxels using a bin size of 5 Å and the number count of ice Ih and Ic bead types (FIG. 3B, voxelizing); this effectively combines the two ice phases and handles the stacking disorder structures in polycrystalline ice. Next, a uniform filter with length=4 voxels (along each axis) is applied to the voxels to improve contrast of the grain boundaries and to minimize noise within the grains (FIG. 3B, uniform filter). Then, a threshold of 3.5 (voxel value) is used to label the voxels as either "voxel at boundary" or "voxel in grain" (FIG. 3B, thresholding).

FIG. 3C shows grain identification using unsupervised machine learning (i.e. clustering). The DBSCAN clustering algorithm with a minimum number of neighbor=27 within a 9 Å neighborhood cutoff, coupled with nearest neighbor search using a periodic k-d tree, identifies individual grains as small and large irregularly-shaped grains from "voxel in grain" (FIG. 3C, DBSCAN+(periodic) k-d tree). DBSCAN is a density-based clustering algorithm. Being an unsupervised machine learning technique, the algorithm automatically determines the number of grains in the system. To provide the best estimate of grain sizes, the periodic k-d tree is used to apply a quick nearest neighbor search to recover "voxel at boundary" that are originally crystalline (including bead type Ih or Ic) and assign to the nearest grain with a priority given to smaller grains (FIG. 3C, nearest neighbor search). k-d tree is used for fast and efficient neighbor searches; time complexity to build is O(n) and to search is O(log n). For simulation data, a periodic k-d tree can be used to handle periodic boundary conditions.

The grains are refined in a final step of the grain identification procedure such that the k-d tree built in the grain identification step is used again to reassign voxels at the boundary (that are originally crystalline) to the nearest grain. This step improves the estimated sizes of the grains and is efficient because the previously built k-d tree may be reutilized. Finally, the voxels are converted back to CG beads by position-based reverse mapping (FIG. 3C, reverse mapping). Thus, this grain identification procedure is utilized on both small and large grains, which are often irregularly-shaped and is robust, fast, and requires minimal user input.

It is important to note that the construction and arrangement of the system shown in the various exemplary implementations is illustrative only and not restrictive in character. All changes and modifications that come within the spirit and/or scope of the described implementations are desired to be protected. For example, while the use of this technology is exemplified for growth of polycrystalline grains of ice from deeply supercooled water to larger crystallites, it should be understood that the present disclosure is not limited to this application. Rather, growth of polycrystalline grains of ice is merely one embodiment meant to exemplify polycrystalline materials in general. The disclosure provided herein may be extended to other polycrystalline materials and/or for other applications. For example, the method disclosed herein may be extended to identify pores and voids as well as cell boundaries in biological systems and connectivity between neurons in brain.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

References herein to the positions of elements (i.e. "top," "bottom," "above," "below," "on," etc.) are merely used to describe the orientation of various elements in the FIGURES. It should be noted that the orientation of various elements may differ according to other exemplary embodiments, and that such variations are intended to be encompassed by the present disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

What is claimed:

1. A method of identifying grains in polycrystalline materials, the method comprising:
   (a) identifying local crystal structure of the polycrystalline material based on neighbor coordination or pattern recognition machine learning, the local crystal structure comprising grains and grain boundaries;
   (b) pre-processing the grains and the grain boundaries using image processing techniques;
   (c) conducting grain identification using unsupervised machine learning; and
   (d) refining a resolution of the grain boundaries.

2. The method of claim 1, wherein the step of identifying local crystal structure is based on neighbor coordination and comprises identifying the atomic structure of a first neighbor of the grains and grain boundaries as at least one of hexagonal close packing (hcp), face-centered cubic (fcc), body-centered cubic (bcc), and icosahedral.

3. The method of claim 2, wherein the step of identifying local crystal structure further comprises identifying the atomic structure of a second neighbor of the grains and grain boundaries as at least one of hexagonal close packing (hcp), face-centered cubic (fcc), body-centered cubic (bcc), and icosahedral.

4. The method of claim 3, wherein the step of identifying local crystal structure generates voxels and a number count of:
   (a) each type of atomic structure for the first neighbor; and
   (b) each type of atomic structure for the second neighbor.

5. The method of claim 1, wherein the step of identifying local crystal structure is based on unsupervised machine learning.

6. The method of claim 4, wherein the step of pre-processing comprises applying a uniform filter to the voxels to reduce noise within the grains and improve contrast of the grain boundaries.

7. The method of claim 4, further comprising labeling the voxels as either in the grain or at the grain boundary.

8. The method of claim 7, wherein the step of conducting grain identification comprises segregating individual grains by classifying the voxels based on grain index and assigning the voxels to be a portion of the grain.

9. The method of claim 8, wherein the step of refining the grains comprises reassigning voxels labeled as at the boundary to its spatially nearest grain.

* * * * *